United States Patent [19]

Hubschmid

[11] Patent Number: 4,526,541
[45] Date of Patent: Jul. 2, 1985

[54] INSTRUMENT FOR THE TREATMENT OF INTERDENTAL SURFACES

[75] Inventor: Walter Hubschmid, Carabietta, Switzerland

[73] Assignee: Walter Hubschmid & Sohn, Viganello, Switzerland

[21] Appl. No.: 513,833

[22] Filed: Jul. 14, 1983

[51] Int. Cl.³ .............................................. A61C 3/02
[52] U.S. Cl. .................................... 433/165; 433/82
[58] Field of Search ................ 433/166, 165, 82, 118, 433/119, 120, 122, 123, 124, 81

[56] References Cited

U.S. PATENT DOCUMENTS

| | | | |
|---|---|---|---|
| 1,354,139 | 9/1920 | Shaw | 433/122 |
| 1,821,079 | 9/1931 | Schultze | 433/166 |
| 2,411,234 | 11/1946 | Silver | 433/122 |
| 2,874,470 | 2/1959 | Richards | 433/165 |
| 3,461,563 | 8/1969 | Nelson | 433/165 |
| 3,552,022 | 1/1971 | Axelsson | 433/124 |
| 4,021,920 | 5/1977 | Kirschner et al. | 433/165 |
| 4,055,897 | 11/1977 | Brix | 433/166 |
| 4,270,903 | 6/1981 | Nash | 433/165 |
| 4,330,278 | 5/1982 | Martin | 433/81 |

Primary Examiner—John J. Wilson
Attorney, Agent, or Firm—Wender Murase & White

[57] ABSTRACT

An instrument for the treatment of interdental surfaces is disclosed. The instrument is adapted for attachment to a bored, reciprocable holder of a driven dental tool which includes a fluid supply conduit in communication with the tool holder. The dental instrument has a flexible blade (3) having at least one diamond abrasive surface (4) bonded thereto. The instrument also has a pair of mutually opposed, bowed ears (2a) attached to the blade adapted for biased insertion into the bored holder so as to secure retention within the holder. The pair of mutually opposed bowed ears also defines a channel therebetween for fluid communication from the holder fluid supply conduit to the abrasive surface. The flexible blade of the dental instrument when combined with the optimal location of the fluid channel for direct communication with the abrasive surface, permits effective treatment of interdental surfaces on both side teeth and front teeth, which helps maintain healthy periodontum tissue necessary for good dental health.

5 Claims, 5 Drawing Figures

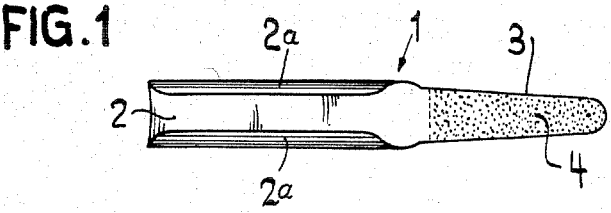
FIG. 1
FIG. 2
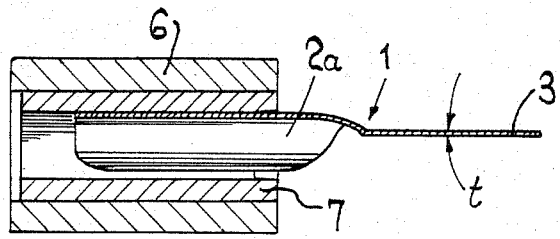
FIG. 3
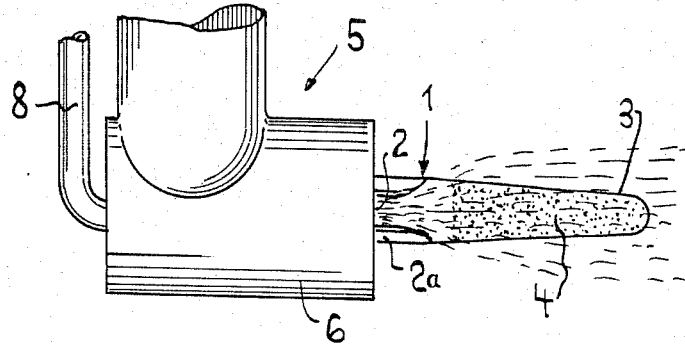
FIG. 4
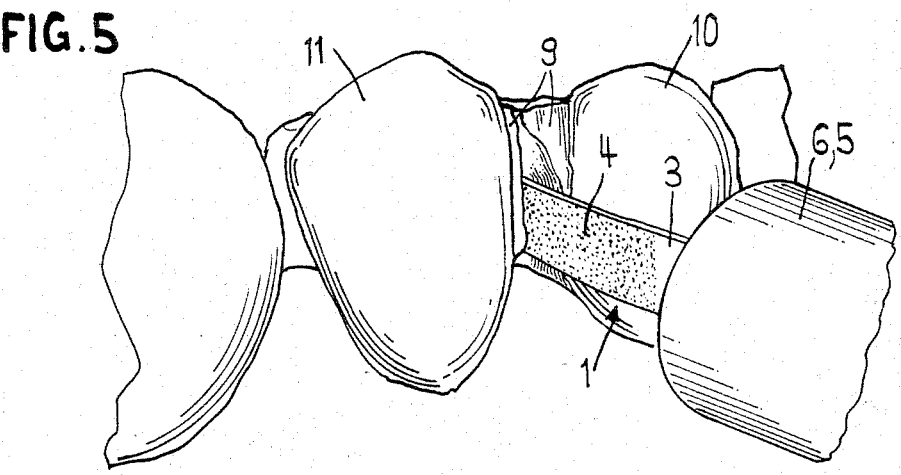
FIG. 5

INSTRUMENT FOR THE TREATMENT OF INTERDENTAL SURFACES

BACKGROUND OF THE INVENTION

The present invention relates to an instrument for the treatment of interdental surfaces, which is plug attachable to on an a power driven dental apparatus, wherein the apparatus has an angle piece in which rotary motion is converted into reciprocating motion and the instrument is removably fixed in the head thereof. Such an apparatus is described in the German Pat. No. 1 766 651 and it is used with a set of instruments with rigid diamond tips having a triangular profile and a full holding part. Water which is required during the utilisation of diamond tips is directed from outside the angle piece against the tip. Diamond tips that are available on the market are coated only with a coarse type of diamond grain.

Another instrument is described in the U.S. Pat. No. 1 354 139 which, however, does not utilize diamond tips and wherein the body of the tip is reinforced and thus rigid.

OBJECT AND BRIEF SUMMARY OF THE INVENTION

It is an object of the present invention to provide an instrument for substantially improved treatment of the interdental surfaces with diamond coated abrasive blades, which enable fine contouring of concave proximal surfaces of tooth filling and crown margins and removal of residues between teeth in narrow interdental spaces.

This object is attained by the instruments described in the herein.

BRIEF DESCRIPTION OF THE DRAWING

The present invention will be described further by way of example and with reference to the accompanying drawing, in which:

FIG. 1 shows a top view on a tip of an instrument constructed in accordance with the teachings of the invention, FIG. 2 shows a frontal view of the tip of FIG. 1, FIG. 3 shows the tip of FIG. 1 inserted into a power driven dental apparatus, FIG. 4 shows a top view of an angle piece of the apparatus of FIG. 3, and FIG. 5 shows schematically how the instruments of the present invention is used.

FIG. 1 shows a tip 1 a set of instruments constructed in accordance with the teachings of the present invention. This tip comprises a hollow through holding part 2 and a blade 3 coated on one side with diamond grain abrasive surface 4. The whole tip consists of a thin steel plate blade, wherein the holding part 2 is formed by a pair of opposed, bowed ears 2a attached to the blade 4, having the form of a not completely closed cylinder. FIG. 4 shows that cylinder functions as a means for directing water to the abrasive surface. Due to its small thickness between approximately 0.1 mm and 0.2 mm and depending on the type of application, this working part is flexible so that it can easily conform itself to the surface contour of a tooth. It also permits working contact with formerly inaccessible interdental surfaces. The best flexibility required for each working process is rendered possible by the choice of the material and the selection of an adequate blade thickness.

In order to obtain perfectly ground and polished proximal surfaces of fillings, and crown margins, which is desired for maintaining the health of the adjacent periodontum, it is necessary use instruments having graduated coarseness of diamond grain abrasive. This ensures that the treatment is adapted to the particular condition of the teeth which may range from removal of coarse residues to the initial polishing. Experiments have shown that a set of instruments consisting of three flexible, one sided diamond coated abrasive surfaced blades and an insert of synthetic material for polishing optimally fulfill the treatment needs.

The first, relatively coarse blade has a thickness (shown as "t" in FIG. 3) of about 0.15 mm to 0.20 mm and also has a diamond coating with a mean size of the grain of about 80 $\mu$m for permitting the removal of large overhanging marginal irritations or the trimming of overcontoured crown margins. The second or middle tip has a blade thickness of about 0.11 mm to 0.15 mm and also has a diamond coating with a mean size of the grains of about 40 $\mu$m and it permits the contouring of the proximal surfaces of fillings and crown margins. The third or fine tip has a thickness of about 0.09 mm to 0.11 mm comprises a diamond coating with a mean size of the grain of about 15 $\mu$m, which allows initial tooth polishing. The fourth instrument is a known plastic insert which permits even without water sparkling but with polishing means to achieve finally a mirror finish.

The diamond abrasive surfaces become rapidly clogged by amalgam which renders them ineffective; the diamond tips must be unclogged by removing the amalgam with a special rubber cleaning block. For cleaning, the amalgam clogged instruments are dried, placed in the handpiece and set in motion against the special rubber cleaning block.

The angle piece 5 shown in FIG. 4 comprises a head 6 in which is arranged a reciprocating moving instrument holder 7 (see FIG. 3). This instrument holder 7 is in form of a hollow cylinder defining a bore in which the holding part 2 of the instrument may be introduced. Due to the fact that the cylindrical holding part 2 is not completely closed, the ears act as a radial biasing member so that firm retention is ensured. As indicated in FIG. 4, a water conduit 8 is led into the head 6 of the angle piece, this conduit opening out and communicating with the bore of the hollow instrument holder 7. Thus the water reaches the hollow instrument holder 7 through the conduit 8 and it reaches the abrasive surface 4 through the channel defined by the holding part 2. Direction of water through the instrument directly to the abrasive surface ensures an optimal lubrication and cooling of the abrasive surface and removal of ground material. The angle piece is mounted in a known manner on a power-driven dental tool (not shown) designed for the treatment of teeth, e.g. a boring instrument. In such a known angle piece the rotating motion of the axle of the apparatus for the treatment of teeth is converted into a reciprocating motion.

FIG. 5 shows a schematic illustration of the treatment of a filling 9 between two teeth 10 and 11 by means of an inserted instrument 1. The dimensions of the drawing are practically true to scale and one sees that the instrument may be introduced between the two teeth for grinding the filling and for obtaining a good oral prophylaxis. One works preferably without any pressure and with an adequate dental tool rotational speed of about 3000 rpm, that is about 6000 reciprocating strokes per minute.

By means of such a power-driven dental tool with an adapted set of instruments, it is possible to remove rationally coarse proximal residues of amalgam or composite, to trim overhanging crown margins of gold or ceramic and this on the side teeth as well as on the front teeth, even in the narrowest interdental spaces, and to polish initially the proximal filling surfaces and crown margins.

It is also possible to utilize a coating with diamond grains having other sizes of the grain. Thus it is possible to utilize for the coarse tips diamond abrasive grains having a mean size of 60 to 120 μm, for the middle tips a mean size of the grain of 30 to 50 μm and for the fine tips a mean size of the grain of 10 to 20 μm.

I claim:

1. An interdental surface treatment apparatus comprising:
    a dental tool having a bored, reciprocable holder and a fluid supply conduit in communication with said holder; and
    a dental instrument having a flexible blade including at least one diamond abrasive surface bonded thereto and a pair of mutually opposed, bowed ears attached to said blade, said ears being biasedly inserted into said reciprocable holder bore, said ears forming a channel therebetween for directing fluid between said fluid supply conduit and said abrasive surface.

2. The dental instrument as recited in claim 1 wherein said blade has a thickness of between approximately 0.09 mm and 0.11 mm and said diamond abrasive surface has mean size grains of between approximately 10 microns and 20 microns.

3. The dental instrument as recited in claim 1 wherein said blade has a thickness of between approximately 0.11 mm and 0.15 mm and said diamond abrasive surface has mean size grains of between approximately 30 microns and 50 microns.

4. The dental instrument as recited in claim 1 wherein said blade has a thickness of between approximately 0.15 mm and 0.20 mm and said diamond abrasive surface has mean size grains of between approximately 60 microns and 120 microns.

5. The interdental surface treatment apparatus as recited in claim 1 wherein said ears each have a first side attached to a first portion of said blade and a second side distal said first side; and said blade has a second portion offset relative to said first portion toward said second sides of said ears and generally parallel to said first portion.

* * * * *